United States Patent [19]

Thome et al.

[11] Patent Number: 5,800,486

[45] Date of Patent: Sep. 1, 1998

[54] DEVICE FOR TRANSURETHRAL THERMAL THERAPY WITH COOLING BALLOON

[75] Inventors: Scott P. Thome, Waite Park; Jim Kauphusman, Champlin, both of Minn.; Mitchell Dann, Jackson, Wyo.

[73] Assignee: Urologix, Inc., Minn.

[21] Appl. No.: 672,504

[22] Filed: Jun. 17, 1996

[51] Int. Cl.⁶ .................................................. A61N 5/02
[52] U.S. Cl. ..................... 607/105; 607/101; 607/102; 607/113; 607/156
[58] Field of Search ..................... 604/96–98, 114, 604/264, 280; 607/101–105, 113, 116, 154, 156

[56] References Cited

U.S. PATENT DOCUMENTS

| | | | |
|---|---|---|---|
| 4,497,324 | 2/1985 | Sullivan et al. | 128/736 |
| 4,601,296 | 7/1986 | Yerushalmi | 238/804 |
| 4,662,383 | 5/1987 | Sogawa et al. | 128/784 |
| 4,676,258 | 6/1987 | Inokuchi et al. | 128/804 |
| 4,823,812 | 4/1989 | Eshel et al. | 128/804 |
| 4,924,863 | 5/1990 | Sterzer | 606/27 |
| 4,932,958 | 6/1990 | Reddy et al. | 606/192 |
| 4,945,912 | 8/1990 | Langberg | 128/642 |
| 4,955,377 | 9/1990 | Lennox et al. | 128/401 |
| 4,961,738 | 10/1990 | Mackin | 606/15 |
| 4,967,765 | 11/1990 | Turner et al. | 128/785 |
| 4,985,028 | 1/1991 | Isner et al. | 606/15 |
| 4,993,430 | 2/1991 | Shimoyama et al. | 129/784 |

(List continued on next page.)

FOREIGN PATENT DOCUMENTS

| | | |
|---|---|---|
| 0 370 890 | 11/1989 | European Pat. Off. . |
| 0 519 958 B1 | 3/1991 | European Pat. Off. . |
| 0 597 463 A2 | 11/1993 | European Pat. Off. . |
| 0 643 982 A1 | 6/1994 | European Pat. Off. . |
| 0 646 359 A1 | 10/1994 | European Pat. Off. . |
| 0 646 360 A1 | 10/1994 | European Pat. Off. . |
| WO 89/05609 | 6/1989 | WIPO . |
| WO 91/11975 | 8/1991 | WIPO . |
| WO 91/13650 | 9/1991 | WIPO . |
| WO 93/20767 | 10/1993 | WIPO . |
| WO 94/02204 | 2/1994 | WIPO . |
| WO 94/07446 | 4/1994 | WIPO . |
| WO 94/26188 | 11/1994 | WIPO . |
| WO 94/28809 | 12/1994 | WIPO . |
| WO 96/00041 | 1/1996 | WIPO . |

OTHER PUBLICATIONS

"Microwave Applicator for Transurethral Hyperthermia of Benign Prostatic Hyperplastic" by M.A. Astrahan et al, *International Journal of Hyperthermia*, 1989, vol. 5, No. 3, 283–296.

"Transurethral Microwave Heating of the Prostate—Or from Hyperthermia to Thermotherapy" by M. Devonec et al., *Journal of Endourology*, vol. 5, No. 2, 1991, 129–135.

"Single–Session Transurethral Microwave Thermotherapy for the Treatment of Benign Prostatic Obstruction" by Carter et al, *Journal of Endourology*, vol. 5, No. 2, 1991, 137–144.

Local Hyperthermia of the Prostate Gland for the Treatment of Benign Prostatic Hypertrophy and Urinary Retention by Linder et al, *Journal of Urology*, 1987, 60, 567–571.

"International Consultation on BPH by WHO. Report of the Subgroup on other Nonmedical Treatment", by Perez–Castro et al, *Arch. Esp. de Urol.* , vol. 45.1, 723–743 (1992).

"Prostatic Thermal Ablation—The T3 System" by Miller et al, *11th Congress of European Association of Urology*, Jul. 13–16, 1994, Berlin Germany.

*Primary Examiner*—Jennifer Bahr
*Assistant Examiner*—Stephen Huang
*Attorney, Agent, or Firm*—Kinney & Lange, P.A.

[57] ABSTRACT

An intraurethral catheter includes an microwave antenna and a cooling lumen structure substantially surrounding the antenna. A cooling balloon partially surrounds the cooling lumens on one side of the catheter adjacent the microwave antenna. The cooling balloon improves wall contact between the catheter and a wall of the urethra to improve cooling of the urethra. The cooling balloon communicates with the cooling lumen structure to permit circulation of cooling fluid through the cooling balloon.

25 Claims, 12 Drawing Sheets

U.S. PATENT DOCUMENTS

| | | | |
|---|---|---|---|
| 4,997,431 | 3/1991 | Isner et al. | 606/15 |
| 5,003,991 | 4/1991 | Takayama et al. | 128/784 |
| 5,007,437 | 4/1991 | Sterzer | 428/786 |
| 5,056,531 | 10/1991 | Shimoyama | 128/784 |
| 5,061,267 | 10/1991 | Zeiher | 606/40 |
| 5,151,100 | 9/1992 | Abele et al. | 606/28 |
| 5,234,004 | 8/1993 | Hascoet et al. | 607/116 |
| 5,246,438 | 9/1993 | Langberg | 606/33 |
| 5,281,212 | 1/1994 | Savage et al. | 606/15 |
| 5,281,217 | 1/1994 | Edwards et al. | 606/41 |
| 5,330,518 | 7/1994 | Neilson et al. | 607/101 |
| 5,334,193 | 8/1994 | Nardella | 606/41 |
| 5,344,435 | 9/1994 | Turner et al. | 607/101 |
| 5,370,678 | 12/1994 | Edwards et al. | 607/101 |
| 5,391,197 | 2/1995 | Burdette et al. | 607/97 |
| 5,413,588 | 5/1995 | Rudie et al. | 607/101 |
| 5,417,689 | 5/1995 | Fine | 606/41 |
| 5,423,811 | 6/1995 | Imran et al. | 606/41 |
| 5,462,521 | 10/1995 | Brucker et al. | 604/20 |
| 5,464,445 | 11/1995 | Rudie et al. | 607/101 |
| 5,465,717 | 11/1995 | Imran et al. | 128/642 |
| 5,471,982 | 12/1995 | Edwards et al. | 128/642 |
| 5,474,071 | 12/1995 | Chapelon et al. | 128/660.03 |
| 5,484,384 | 1/1996 | Fearnot | 600/3 |
| 5,484,433 | 1/1996 | Taylor et al. | 606/17 |
| 5,485,849 | 1/1996 | Panescu et al. | 128/699 |
| 5,487,740 | 1/1996 | Sulek et al. | 606/15 |
| 5,509,929 | 4/1996 | Hascoet et al. | 607/101 |
| 5,522,873 | 6/1996 | Jackman et al. | 607/122 |
| 5,545,137 | 8/1996 | Rudie et al. | 607/101 |
| 5,628,770 | 5/1997 | Thome et al. | 607/101 |
| 5,649,973 | 7/1997 | Tierney et al. | 607/101 |

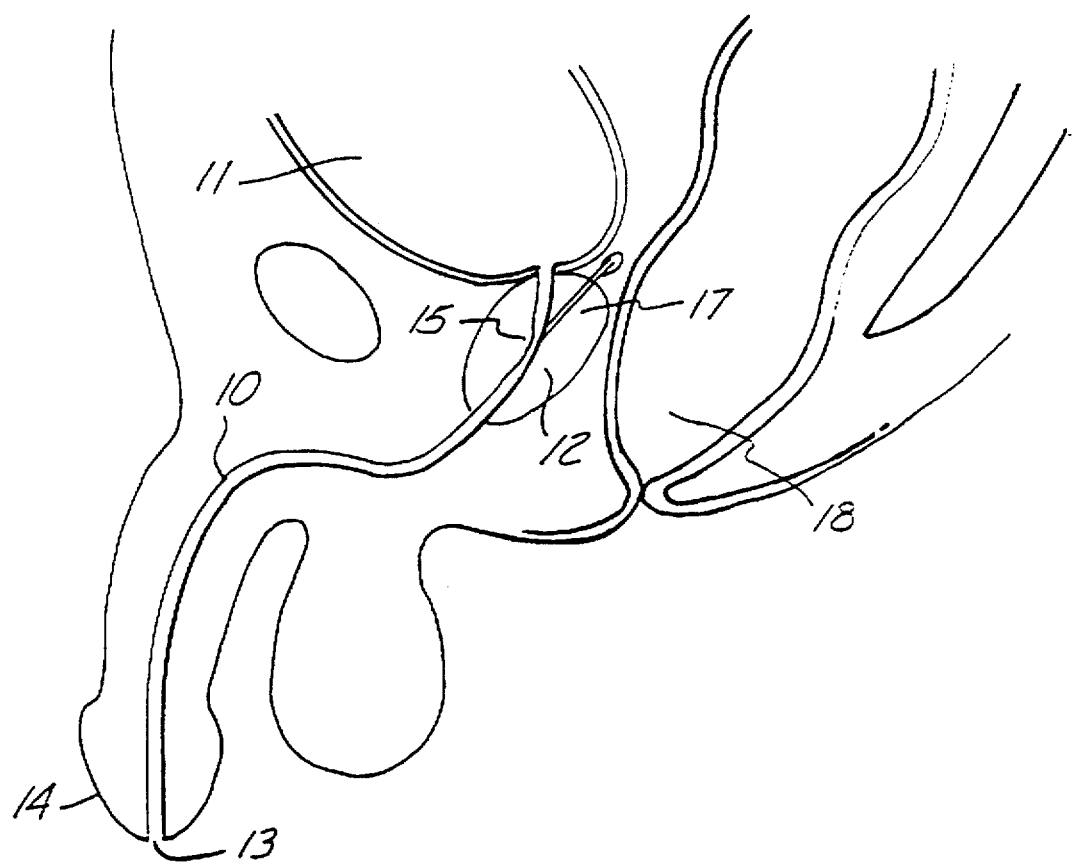

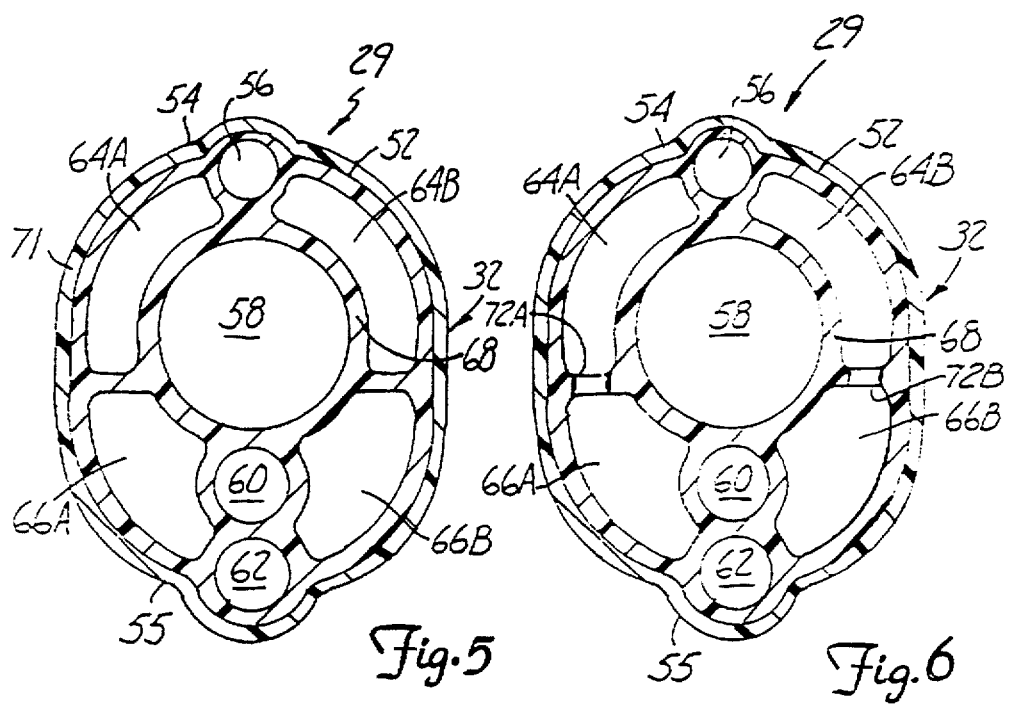

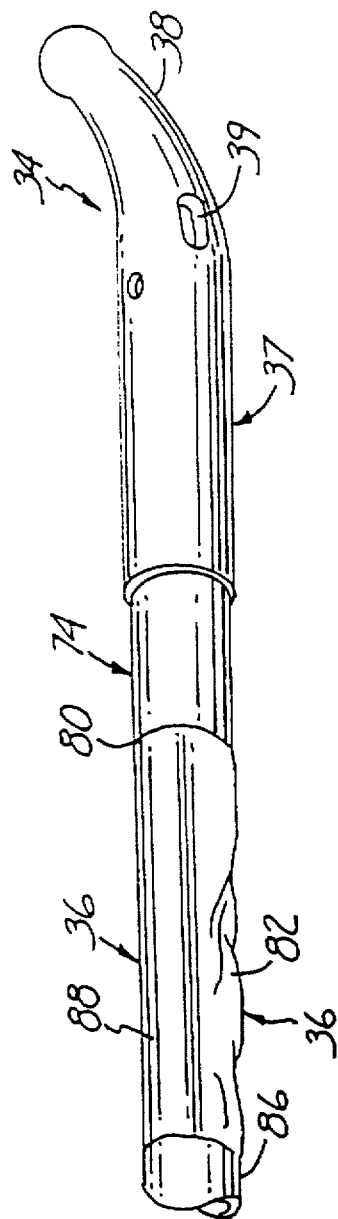
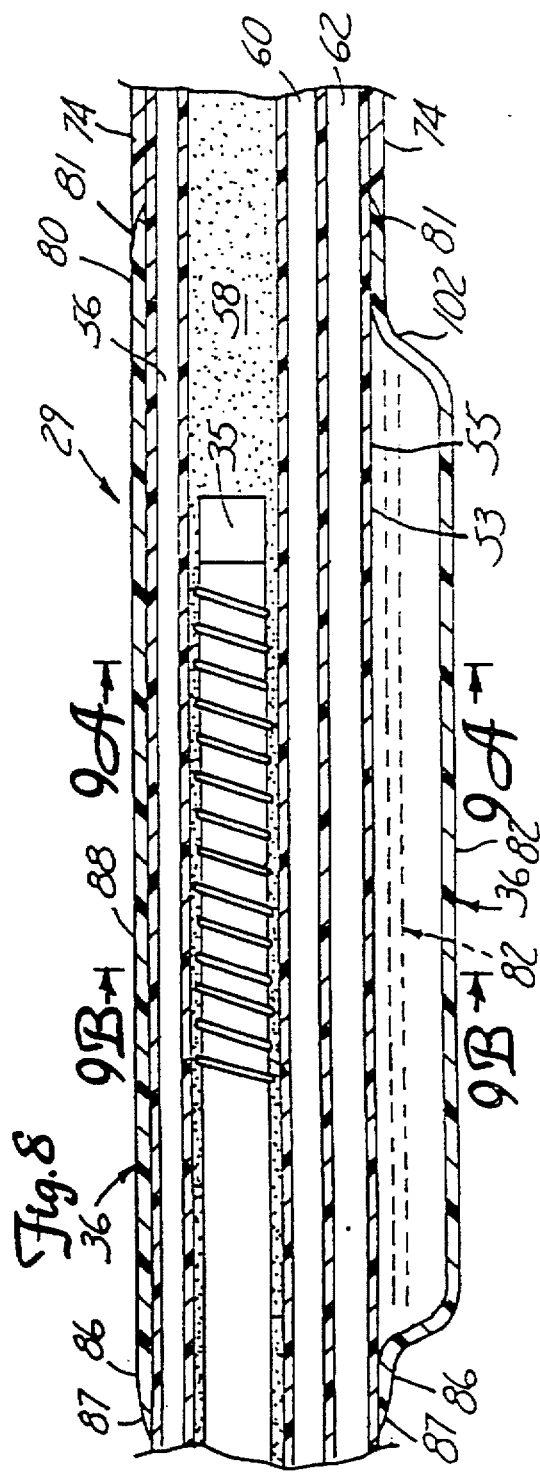

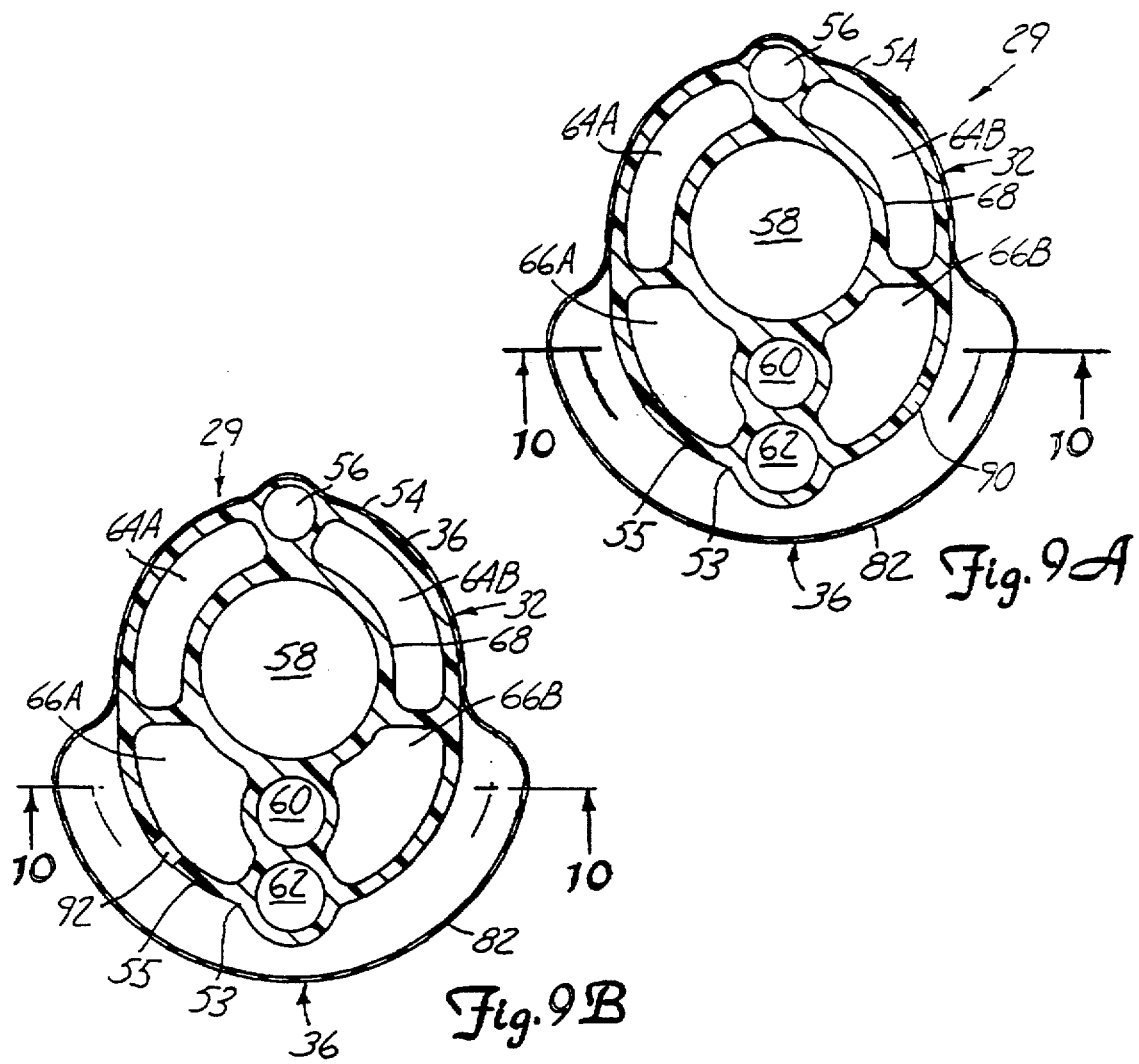

DEVICE FOR TRANSURETHRAL THERMAL THERAPY WITH COOLING BALLOON

REFERENCE TO CO-PENDING APPLICATIONS

Reference is hereby made to copending application Ser. No. 08/469,201, filed Jun. 6, 1995, application Ser. No. 08/413,392, filed Mar. 30, 1995, and application Ser. No. 08/664,363, titled ARTERIAL MICROWAVE APPLICATOR WITH COOLING, filed concurrently herewith.

BACKGROUND OF THE INVENTION

The present invention relates to the field of microwave thermal therapy of tissue. In particular, the present invention relates to a catheter for transurethral microwave thermal therapy of diseased tissue adjacent a conduit such as therapy of benign prostatic hyperplasia (BPH).

The prostate gland is a complex, chestnut-shaped organ which encircles the urethra immediately below the bladder. This relatively small organ, which is the most frequently diseased of all internal organs, is the site of a common affliction among older men, benign prostatic hyperplasia (BPH), as well as a more serious affliction, cancer. BPH is a nonmalignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Recent treatment of BPH includes transurethral microwave thermal therapy in which microwave energy is employed to elevate the temperature of tissue surrounding the prostatic urethra above about 45° C., thereby thermally damaging the tumorous BPH tissue. Transurethral catheters used in microwave thermal therapy can include cooling systems arranged about a microwave antenna. These cooling systems protect surrounding healthy tissues by selectively absorbing microwave radiation and minimize thermal damage to the urethral wall by absorbing heat energy via thermal conduction. As a consequence, pain associated with thermal damage during the application of microwave radiation to the prostate is minimized. Ideally, the cooling system and the urethral wall are maintained in contact to insure adequate cooling of the urethral wall.

However, the geometry of the urethra hinders the ability to maintain uniform contact between the cooling system and the urethral wall. For example, the portion of the urethra extending through the prostate (i.e., the prostatic urethra) includes a distal segment and a proximal segment. The distal segment extends at an angle relative to the proximal segment forming a point of angulation at approximately the midpoint of the prostatic urethra. In addition, an inner surface of the distal segment of the prostatic urethra includes a small protrusion called the verumontanum. The juxtaposition of the point of angulation and the protruding verumontanum hinder establishing uniform contact between a cooling system of a catheter and the urethral wall in this region. The prostatic urethra also has a generally triangular shaped transverse cross section prior to catheter insertion which can also complicate establishing uniform contact between an outer surface of a catheter and the urethral wall to insure adequate cooling of the urethra.

SUMMARY OF THE INVENTION

A catheter of the present invention is adapted for insertion into a urethra and preferably includes a microwave antenna, a cooling lumen structure, and an inflatable cooling balloon. The microwave antenna delivers necrosing levels of microwave energy to diseased prostatic tissue spaced from the catheter. The cooling lumen structure surrounds the antenna and cools tissues immediately surrounding the catheter while selectively absorbing microwave energy emitted by the antenna to achieve a preferential heating pattern in the prostatic tissue surrounding the catheter. The cooling balloon of the catheter is positioned adjacent the antenna and partially surrounds the cooling lumen structure on one side of the catheter to provide additional tissue cooling and microwave energy absorption on the side of the catheter opposite the target tissue. The cooling balloon is adapted to cause uniform wall contact between the outer surface of the catheter and the varying geometry of the urethral wall to insure adequate cooling of the urethra along its length. By improving urethral wall contact and by bolstering the microwave radiation absorption and tissue cooling capability of one side of the catheter with a cooling balloon of the catheter of the present invention, greater necrosing temperatures can be applied in intraprostatic tissues adjacent an opposite side of the catheter to achieve an improved preferential heating pattern.

BRIEF DESCRIPTION OF THE DRAWINGS

FIG. 1 is a vertical sectional view of a male pelvic region showing the urinary organs affected by benign prostatic hyperplasia.

FIG. 5 is a cross-sectional view of the urethral catheter of FIG. 4 taken along line 5—5.

FIG. 6 is a cross-sectional view of the urethral catheter of FIG. 4 taken along line 6—6.

FIG. 7 is a perspective view of a combined tip, retention balloon, and cooling balloon of the urethral catheter of the present invention.

FIG. 8 is an enlarged sectional view of the proximal end of the urethral catheter of the present invention.

FIG. 9A is a sectional view of the catheter shaft of FIG. 4 taken along lines 9A—9A.

FIG. 9B is a sectional view of the catheter shaft of FIG. 4 taken along lines 9B—9B.

DETAILED DESCRIPTION OF THE PREFERRED EMBODIMENTS

Figure 3:
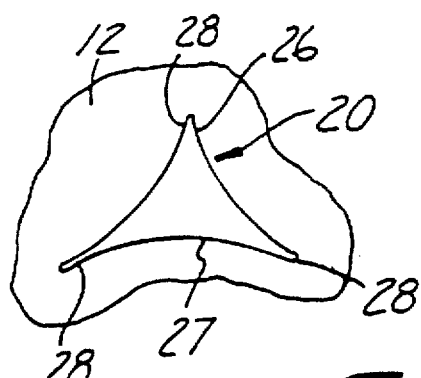
FIG. 3 is a sectional view of a urethra of FIG. 2 as seen along the lines 3—3.

FIG. 1 is a vertical sectional view of a male pelvic region showing the effect benign prostatic hyperplasia (BPH) has on the urinary organs. Urethra 10 is a duct leading from bladder 11, through prostate 12 and out orifice 13 of penis end 14. Benign tumorous tissue growth within prostate 12 around urethra 10 causes constriction 15 of urethra 10, which interrupts the flow of urine from bladder 11 to orifice 13. The tumorous tissue of prostate 12 which encroaches urethra 10 and causes constriction 15 can be effectively removed by heating and necrosing the encroaching tumorous tissue. Ideally, with the present invention, periurethral tumorous tissue of prostate 12 anterior and lateral to urethra 10 is heated and necrosed while avoiding unnecessary and undesirous damage to urethra 10 and to adjacent healthy tissues, such as ejaculatory duct 17 and rectum 18. A selective heating of benign tumorous tissue of prostate 12 (transurethral thermal therapy) is made possible by a microwave antenna-containing catheter of the present invention, shown later in FIGS. 4–10.

Figure 2:
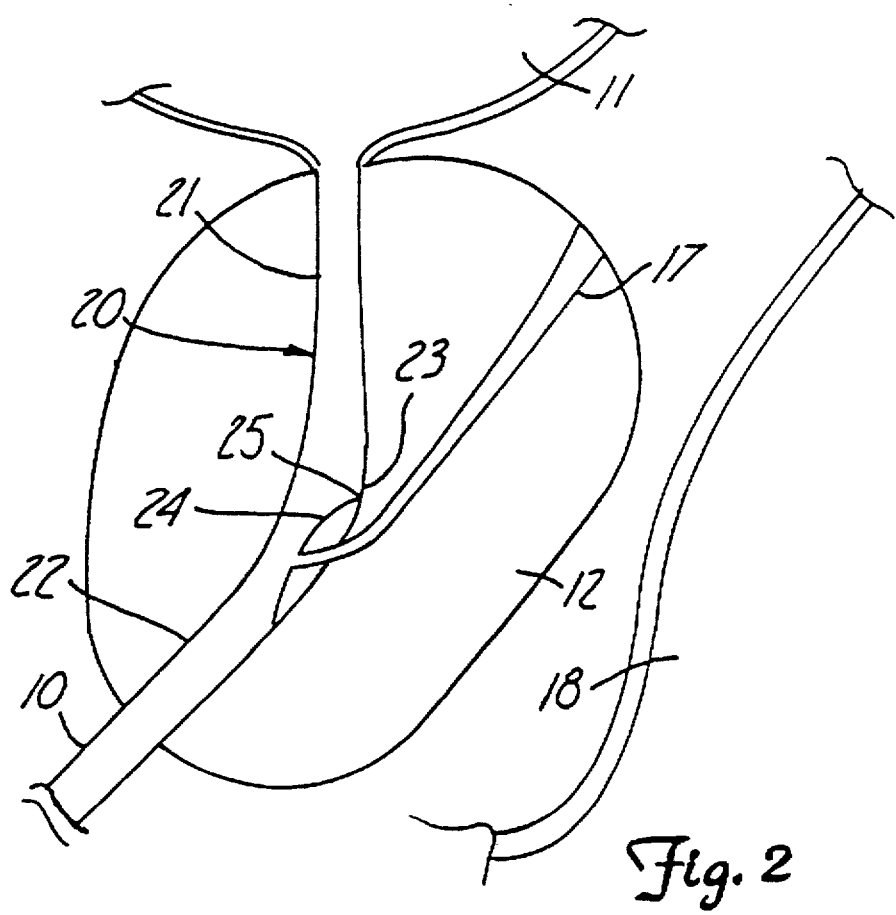
FIG. 2 is a vertical sectional view of a urethra extending through a prostate.

FIG. 2 is sectional view of prostate 12 illustrating specific anatomical features of urethra 10 in prostate 12. Prostatic urethra 20 includes proximal segment 21, distal segment 22, point of angulation 23, and verumontanum 24. Proximal segment 21 extends from point 23 to bladder 11 while distal segment 22 extends from point 23 to the remaining distal portion of prostate 12. Verumontanum 24 is located in distal segment 22 of prostatic urethra 20 adjacent to and just distal to point of angulation 23. Verumontanum 24 forms a protrusion on the wall of prostatic urethra 20. Ejaculatory duct 17 extends through verumontanum 24 and is exposed in distal segment 22 of prostatic urethra 20. Verumontanum 24 effectively creates a constriction in distal segment 22 and in combination with point of angulation 23 creates recess 25 at the junction between the distal and proximal segments. Contact between an outer surface of a catheter and the urethral wall can be compromised in this recess region 25 of prostatic urethra 20 just proximal to verumontanum 24).

Prostatic urethra 20 also has other anatomical features hindering uniform wall contact between an outer surface of a catheter and a urethral wall. FIG. 3 is a cross-sectional view of prostatic urethra 20 taken along line 3—3 of FIG. 2. As shown in FIG. 3, prostatic urethra 20 has a generally triangular shaped transverse cross-section and includes anterior portion 26, and posterior portion 27 and vertices 28. Prostatic urethra 20 expands when fluid (e.g. urine) passes through the urethra, or when a catheter extends through urethra 10. In the latter case, a significant majority of the wall of prostatic urethra 20 establishes contact with an outer surface of a catheter. However, an intraurethral catheter typically is positioned within urethra 10 so that the catheter is closer to anterior portion 26 of prostatic urethra 20 (adjacent the nearest vertex 28) than posterior portion 27. In some cases, sufficient contact is not established between the outer surface of the catheter and posterior portion 27 of urethra 10 along the length of prostatic urethra 20 and between the outer surface of the catheter and vertices 28 adjacent posterior portion 27 of prostatic urethra 20.

Figure 4:
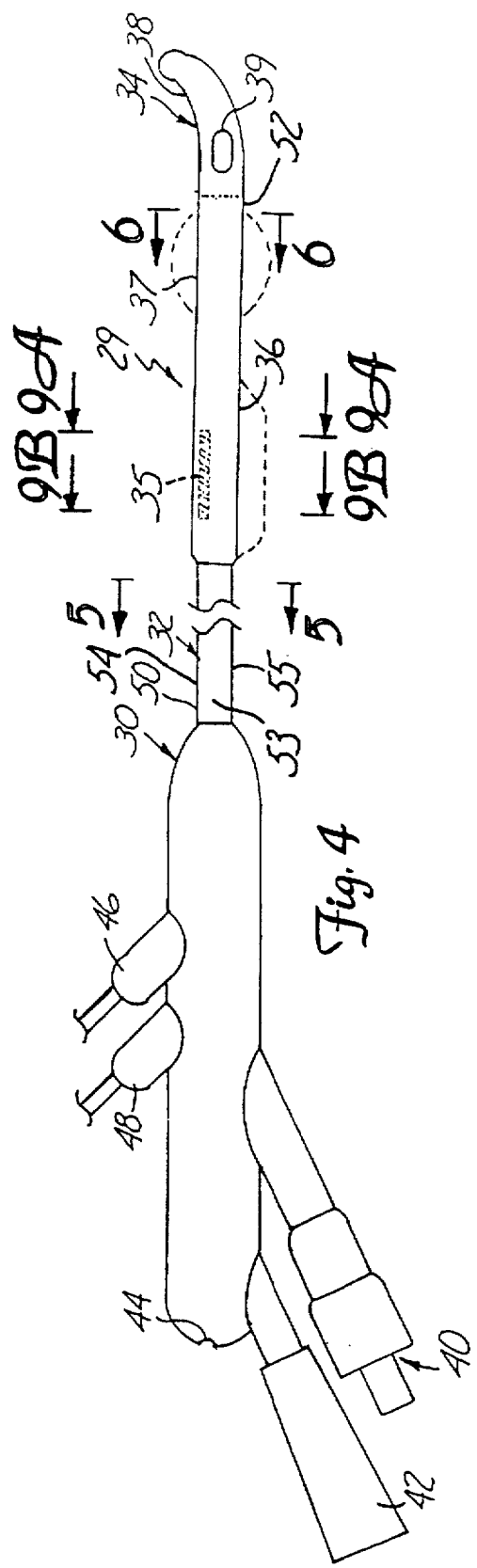
FIG. 4 is a plan view of the urethral catheter of the present invention.

A microwave antenna-containing catheter 29 of the present invention, shown in FIGS. 4–10, includes a cooling balloon especially adapted for urging an outer surface of the catheter into intimate contact with prostatic urethra 20 and for insuring protection of healthy tissues adjacent the catheter. As shown in FIG. 4, catheter 29 generally includes multi-port manifold 30, multi-lumen shaft 32, tip 34, and microwave antenna 35. Tip 34 includes cooling balloon 36, retention balloon 37, tip portion 38, and side port 39. Manifold 30 includes inflation port 40, urine drainage port 42, microwave antenna port 44, cooling fluid intake port 46, and cooling fluid exhaust port 48. Ports 4–48 of manifold 30 communicate with corresponding lumens within shaft 32. Catheter 29 can be employed in a thermal therapy catheter system further including a cooling system, a microwave generating source, and a urethral thermometry unit. These additional elements of a thermal therapy catheter system are disclosed in Rudie et al. U.S. Pat. No. 5,413,588, which is hereby incorporated by reference.

Catheter shaft 32 includes distal end 50, proximal end 52, and outer surface 53 having first side 54 and second side 55. When catheter 29 is placed within a urethra, first side 54 is oriented anteriorly and second side 55 is oriented posteriorly toward rectum 18 (shown in FIG. 1). Shaft 32 is connected to manifold 30 at shaft distal end 50 and is long enough to permit insertion of retention balloon 37 through urethra 10 and into bladder 11. Manifold 30 and multi-lumen shaft 32 are preferably extruded of medical-grade silicone sold by Dow Corning under the trademark Silastic® type Q7-4850, and type Q7-4780, respectively. Alternative materials can include a polystyrene material sold by Advanced Elastomer Systems, L.P. under the trademark Santoprene®. The material of manifold 30 and shaft 32 preferably has a Shore D hardness between 50D and 80D. Catheter shaft 32 can also include several radiopaque markers disposed adjacent proximal end 52 adjacent cooling balloon 36 to facilitate positioning of catheter 29 within prostatic urethra 20 via fluoroscopy.

Cooling balloon 36 is positioned adjacent proximal end 52 of catheter shaft 32 on shaft second side 55 alongside microwave antenna 35, which extends within shaft 32. Cooling balloon 36 is provided so that, when filled with a cooling fluid, cooling balloon 36 prevents unwanted heating of tissue on second side 55 of catheter 29 adjacent to rectum 18 (shown in FIG. 1) while microwave energy radiating from microwave antenna 35 heats tumorous prostatic tissue adjacent to first side 54 of catheter 29. The cooling balloon 36 also improves contact between the catheter and the urethra to reduce blanching of urethral tissue, thereby reducing pain and alleviating the need for anesthesia during treatment.

Cooling balloon 36 operates in conjunction with multi-lumen shaft 32. As shown in FIG. 5, multi-lumen shaft 32 includes temperature sensing lumen 56, microwave antenna lumen 58, urine drainage lumen 60, retention balloon inflation lumen 62, cooling fluid intake lumens 64A and 64B, and cooling fluid exhaust lumens 66A and 66B. The multi lumen shaft 32 is fully described in detail in assignee's copending application U.S. Ser. No. 08/469,201, filed Jun. 6, 1995, titled DEVICE FOR TRANSURETHRAL THERMAL THERAPY, which is hereby incorporated by reference.

Temperature sensing lumen 56 is positioned near first side 54 of shaft 32 and is configured to permit insertion of a thermometry sensor within shaft 32 to monitor the temperature adjacent to first side 54 when shaft 32 is inserted within urethra 10. Microwave antenna lumen 58 is positioned eccentric to the longitudinal axis of catheter shaft 32, antenna lumen 58 being positioned nearer shaft first side 54 than shaft second side 55. Microwave antenna lumen 58 is adapted for receiving microwave antenna 35 to be permanently positioned within antenna lumen 58 of shaft 32 near cooling balloon 36 (FIG. 4) so that antenna 35 will be generally situated adjacent to prostate 12 when shaft 32 is properly positioned within urethra 10. A microwave antenna suitable for incorporation into catheter 29 of the present invention is disclosed in Rudie et al. U.S. Pat. No. 5,413,588, issued May 9, 1995, and is hereby incorporated by reference.

Urine drainage lumen 60 is positioned adjacent antenna lumen 58 between antenna lumen 58 and shaft second side 55. Urine drainage lumen 60 communicates with urine drainage port 42 of manifold 30 at distal shaft end 50 and with side port 39 of tip 34 at proximal shaft end 52 to define a drainage path for urine when tip 34 of catheter 29 is inserted within bladder 11. Retention balloon inflation lumen 62 is positioned near second side 55 of shaft 32, generally between urine drainage lumen 60 and second side 55. Retention balloon inflation lumen 62 communicates with inflation port 40 of manifold 30 to permit inflation and deflation of retention balloon 37.

As shown in FIG. 5, multi-lumen catheter shaft 32 also includes cooling fluid intake lumens 64A, 64B and cooling fluid exhaust lumens 66A, 66B. Cooling lumens 64A–66B surround antenna lumen 58, so that when filled with a cooling fluid, heat energy generated by microwave energy is conducted away from tissues immediately surrounding catheter shaft 32 via thermal conduction and microwave energy emitted by microwave antenna 35 is selectively absorbed.

Cooling fluid intake lumens 64A, 64B are positioned adjacent to shaft first side 54, between first side 54 and antenna lumen 58 while cooling fluid exhaust lumens 66A, 66B are positioned adjacent to shaft second side 55 between second side 55 and antenna lumen 58. Both cooling fluid intake lumens 64A, 64B, and cooling fluid exhaust lumens 66A, 66B extend from shaft distal end 50 to shaft proximal end 52 where each of the lumens 64A,64B,66A,66B terminate. Cooling fluid intake lumens 64A, 64B and cooling fluid exhaust lumens 66A, 66B preferably have a generally arc-shaped transverse cross-section configured to partially surround antenna lumen 58. In combination, cooling lumens 64A, 64B and cooling lumens 66A, 66B substantially surround antenna lumen 58 about a substantial majority (about 75%) of a circumference of antenna lumen 58. Cooling lumens 64A, 64B and 66A, 66B are defined by single wall 68 and have a wall thickness of 0.009 inches. The cooling exhaust lumens 66A, 66B preferably have a radial thickness greater than a radial thickness of the cooling intake lumens 64A, 64B. For example, the cooling intake lumens 64A, 64B preferably have a radial thickness of 0.028 inches and the cooling exhaust lumens 66A, 66B preferably have a radial thickness from about 0.28 inches (adjacent cooling intake lumens 64A,64B) to about 0.037 inches (adjacent urine drainage lumen 60).

As shown in FIG. 6, cooling fluid intake lumens 64A and 64B are in communication with cooling exhaust lumens 66A and 66B, respectively, near proximal shaft end 52 of catheter shaft 32 adjacent retention balloon 37 (FIG. 4). In particular, hole 72A defined in wall 68 between cooling intake lumen 64A and cooling exhaust lumen 66A permits communication between the respective lumens 64A and 66A. Similarly, hole 72B defined in wall 68 between cooling intake lumen 64B and cooling exhaust lumen 66B permits communication between the respective lumens 64B and 66B. Lumens 56–66B, except for urine drainage lumen 60, are all sealed shut proximal to holes 72A, 72B.

Cooling intake lumens 64A and 64B and cooling exhaust lumens 66A and 66B cooperate with a cooling system (not shown) via ports 44 and 46 of manifold 30 to provide a selectively controlled flow of fluid through cooling lumens 64A, 64B, 66A, and 66B during a treatment session. Cooling fluid circulating through cooling lumens 64A–66B carries heat away from tissues immediately surrounding catheter shaft 32 and selectively absorbs microwave energy radiating from microwave antenna 35. In one embodiment, intake lumens 64A, 64B and exhaust lumens 66A, 66B are supplied with cooling fluid from a cooling system via manifold 30. Water from the cooling system is chilled and pumped through cooling fluid intake lumens 64A, 64B toward proximal shaft end 52. Under fluid pressure, water enters cooling fluid exhaust lumens 66A, 66B through holes 72A, 72B and returns to the cooling system through exhaust lumens 66A, 66B for re-chilling and re-circulation.

The cooling exhaust lumens 66A, 66B are relatively larger in cross section than the cooling intake lumens 64A, 64B resulting in more microwave energy being absorbed and greater urethral wall cooling on the second side 55 of the catheter 29 adjacent the cooling exhaust lumens 66A, 66B. This cooling lumen configuration in cooperation with microwave antenna 35 produces a desired preferential heating pattern within prostate 12 when catheter 29 is within urethra 10.

Cooling balloon 36 comprises a portion of tip 34, which is secured onto proximal end 52 of shaft 32. As shown in FIG. 7, tip 34 comprises a single member including cooling balloon 36, transition portion 74, retention balloon 37, and tip portion 38. Retention balloon 37 is a flexible tubular portion while tip portion 38 comprises a flexible curved body. Cooling balloon 36 is located just distally from retention balloon 37 and is spaced from retention balloon 37 so that cooling balloon 36 generally lies adjacent to prostate 12 when retention balloon 37 is inflated within bladder 11. Cooling balloon 36 is a flexible tubular member that includes proximal end 80, expandable portion 82, distal end 84, and connection portion 86. Expandable portion 82 can be inflated and deflated (shown in FIG. 7) by the selective introduction and removal of an inflation fluid within an interior of expandable wall portion 82.

Tip portion 38 and retention balloon 37 of tip 34 are formed by liquid injection molding from a flexible, medical-grade silicone sold by Dow Corning under the trademark Silastic® Q-7-4720, or a similar material such as a thermoplastic elastomer sold under the trademark Santoprene®, Kraton® or Pebax®. The silicone preferably has a material hardness of 20 Shore A, which is relatively soft to provide an atraumatic tip. Tip 34 can also include a radiopaque filler such as barium sulfate added to the silicone material to make tip 34 observable under fluoroscopy.

Cooling balloon 36 is preferably made of polyethylene terephalate, or another high strength cross-linked thermoplastic material capable of permitting low compliant expansion. Cooling balloon 36 is connected directly to shaft 32 and is also preferably connected to retention balloon 37 via transition portion 74 using techniques known to those in the art.

FIG. 8 provides a more detailed view of cooling balloon 36 and catheter shaft 32 at proximal shaft end 52. Cooling balloon 36 surrounds catheter shaft 32 adjacent microwave antenna 35. Cooling balloon 36 is positioned so that connection portion 88 is adjacent shaft first side 54 and expandable portion 82 is adjacent shaft second side 55. Proximal end 80 further defines proximal waist 81 for securing cooling balloon 36 onto shaft 32 and is positioned adjacent transition portion 74 proximal to antenna 35. Distal end 86 further defines distal waist 87 for securing cooling balloon 36 onto shaft 32 and is positioned distal to antenna 35.

Cooling balloon 36 is secured onto proximal shaft end 52 of shaft 32 with an adhesive. Proximal waist 81 of cooling balloon 36 is adhesively bonded to catheter shaft outer surface 53, and distal waist 87 of cooling balloon 36 is adhesively bonded to catheter shaft outer surface 53. In addition, an inner surface of connection portion 88 is adhesively bonded to catheter shaft outer surface 53. Proximal waist 81 is also preferably joined to transition portion 74 using techniques known in the art.

This arrangement creates a sealed connection at distal end 86, proximal end 80, and along connection portion 88 to secure cooling balloon 36 on catheter shaft 32. An inner surface of expandable portion 82 is spaced from and is not secured to shaft outer surface 53 so that expandable portion 82 remains free to expand relative to catheter outer surface 53 upon introduction and passage of an inflation cooling fluid (from cooling lumens 66A, 66B as shown in FIGS. 9A and 9B) through an interior of cooling balloon 36. With cooling balloon 36 secured in this manner, outer surface 53 of catheter second side 55 and expandable portion 82 effectively define a cooling chamber. Expandable portion 82 of cooling balloon 36 is positioned adjacent to microwave antenna 35 so that in use, cooling fluid within cooling balloon 36 will be capable of urging the cooled surfaces of shaft 32 and balloon 36 into intimate contact with the urethral wall and of absorbing additional microwave energy when antenna 35 is energized.

Cooling balloon 36 extends for a length adjacent proximal shaft end 52 that is substantially less than the length of catheter shaft 32, yet equal to or greater than a length of microwave antenna 35. Moreover, cooling balloon 36 has a length less than an entire length of prostatic urethra 20 (shown in FIG. 2) and preferably a length less than or equal to a length of prostatic urethra 20 that extends proximal to verumontanum 24. For example, to accommodate different size prostates, cooling balloon 36 has a length of about 1.0 to 4.0 centimeters with expandable portion 82 having a length of about 1.0 to 3.5 centimeters. In a preferred embodiment, cooling balloon 36 has a length of about 3.0 centimeters and expandable portion 82 has a length of about 2.5 centimeters.

Cooling balloon 36 is further shown in cross section in FIGS. 9A–9B, which are cross-sectional views of shaft 32 taken along lines 9A—9A and 9B—9B in FIG. 4. FIGS. 9A and 9B illustrate the manner in which cooling balloon 36 communicates with cooling lumens 66A, 66B. Cooling balloon 36 surrounds shaft outer surface 53 on shaft second side 55 with expandable portion 82 preferably having a generally arc shaped transverse cross-section (when inflated) which substantially surrounds entire second side 55 including cooling fluid exhaust lumens 66A, 66B. Cooling balloon 36 has a transverse cross-sectional area substantially greater than the transverse cross-sectional area of cooling exhaust lumens 66A, 66B. Alternatively, the cooling balloon 36 is configured to only partially surround a second side 55 of the shaft and to have a cross sectional area equal to or less than a cross-sectional area of cooling exhaust lumens 66A, 66B. Cooling balloon 36 has a wall thickness of about 0.0005 to 0.005 inches, which is substantially less than a wall thickness of wall 68 defining cooling lumens 64A–66B. The cooling chamber defined between catheter outer surface 53 and expandable portion 82 of cooling balloon 36 has a radial thickness of about 0.5 to 5.0 millimeters, which is less than a radial thickness of cooling exhaust lumens 66A, 66B.

Figure 10:
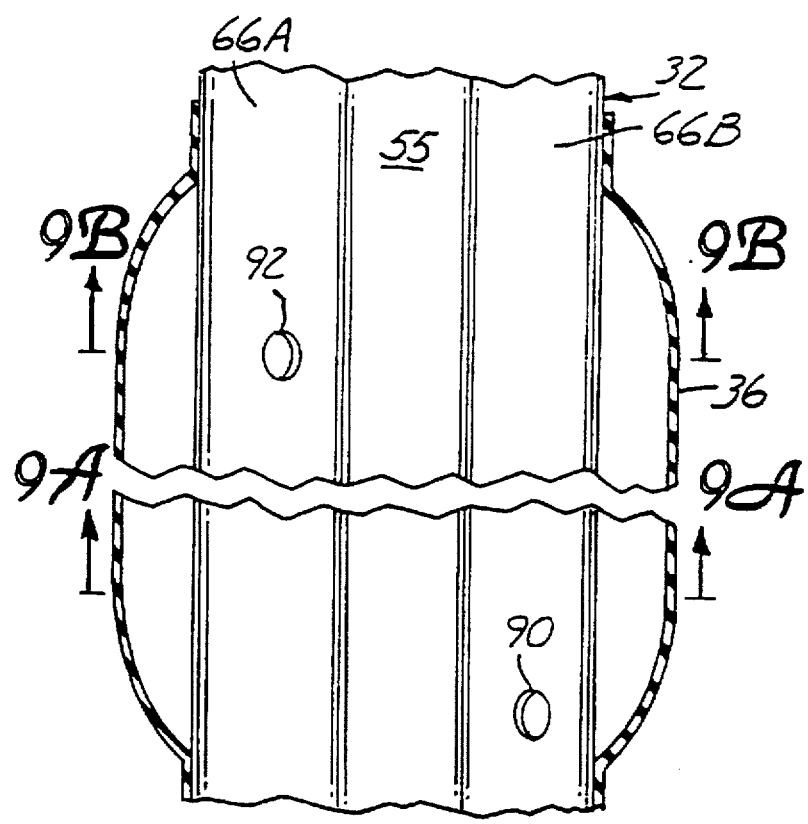
FIG. 10 is a plan view of a second side of the catheter shaft shown in FIGS. 9A and 9B with a balloon portion removed and as taken along lines 10—10.

As shown in FIG. 9A, side wall 68 of catheter shaft 32 defines exhaust lumen 66B including hole 90 and as shown in FIG. 9B, defines exhaust lumen 66A including hole 92. Hole 90 permits communication between cooling exhaust lumen 66B and an interior of cooling balloon 36 and hole 92 permits communication between an interior of cooling balloon 36 and exhaust lumen 66A. Since fluid within cooling lumens 66A and 66B is flowing under pressure distally along catheter shaft 32, fluid within lumen 66B enters inflatable cooling balloon 36, passes through cooling balloon 36 and exits into exhaust lumen 66A to recirculate through a cooling system via manifold 30. As shown in FIG. 10, holes 90 and 92 are axially spaced apart and are laterally spaced apart. This arrangement creates a pressure differential between the respective holes 90 and 92 causing a passive inflation of the cooling balloon 36 and insuring that adequate fluid circulation will occur through cooling balloon 36 as cooling fluid moves through cooling lumens 64A, 64B and 66A, 66B.

In addition, the rate of cooling fluid intake into lumens 64A, 64B and the rate of cooling fluid exhaust out of lumens 66A, 66B can be manipulated by a cooling system via manifold 30 to selectively modify the fluid pressure gradient between hole 90 and hole 92 to maintain cooling balloon 36 in an inflated state and to insure a constant flow of cooling fluid therethrough. The relative sizing of holes 90 and 92, respectively, also can be modified to control the flow of cooling fluid in and out of the cooling balloon 36. For example, hole 90 can be made larger than hole 92 to accentuate filling of cooling balloon 36.

Figure 11:
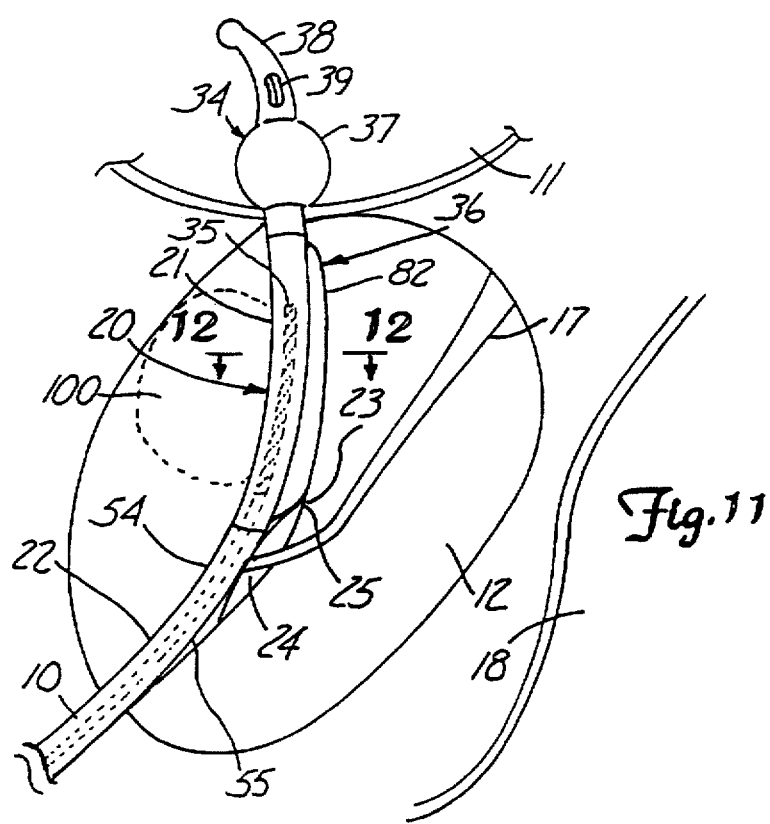
FIG. 11 is a vertical sectional view of a urethra of FIG. 2 shown with a catheter of the present invention positioned therein.
Figure 13:
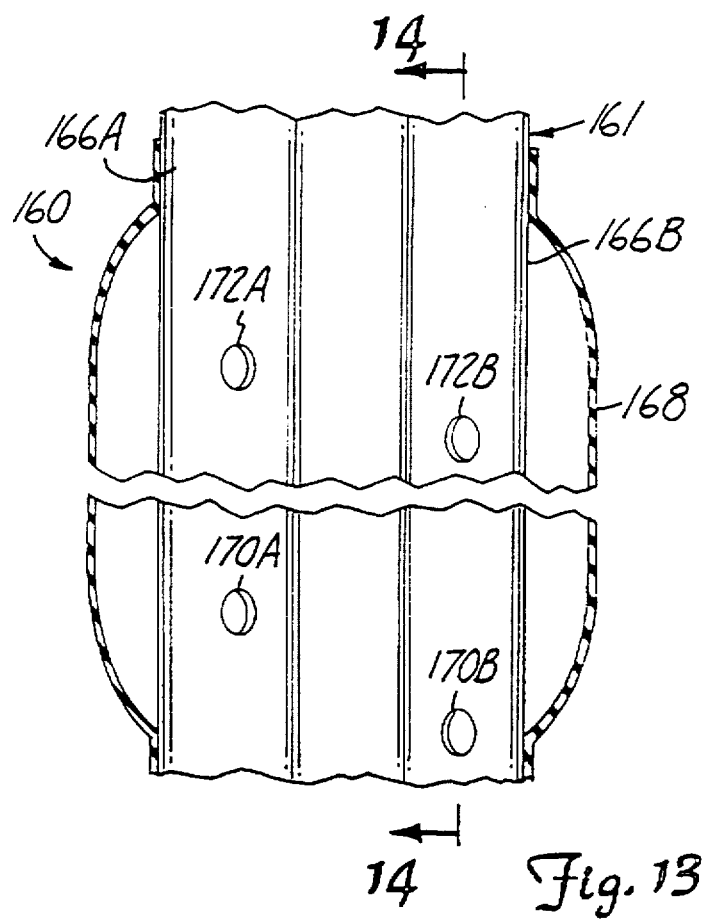
FIG. 13 is a plan view of a second side of the catheter shaft shown in FIGS. 9A and 9B with a balloon portion removed and as taken along lines 10—10, except illustrating an alternate embodiment of cooling exhaust lumens of the catheter of the present invention.

FIG. 11 shows an enlarged view of the male pelvic region of FIG. 1 with catheter 29 properly positioned for use within urethra 10. Shaft 32 is positioned within prostatic urethra 20 with second side 55 of shaft 32 and cooling balloon 36 oriented posteriorly, toward rectum 18 and ejaculatory duct 17. With catheter 29 in this position, a method of ablating tumorous prostatic tissue begins by operating a cooling system to provide a continuous flow of cooling fluid (via manifold 30) through cooling fluid intake lumens 64A, 64B, cooling fluid exhaust lumens 66A, 6613, and cooling balloon 36. Cooling balloon 36, which is shown in an inflated state, is inflated by the introduction and continuous circulation of fluid through cooling balloon 36 via holes 90 and 92 (see FIGS. 9A, 9B, and 10).

Figure 12:
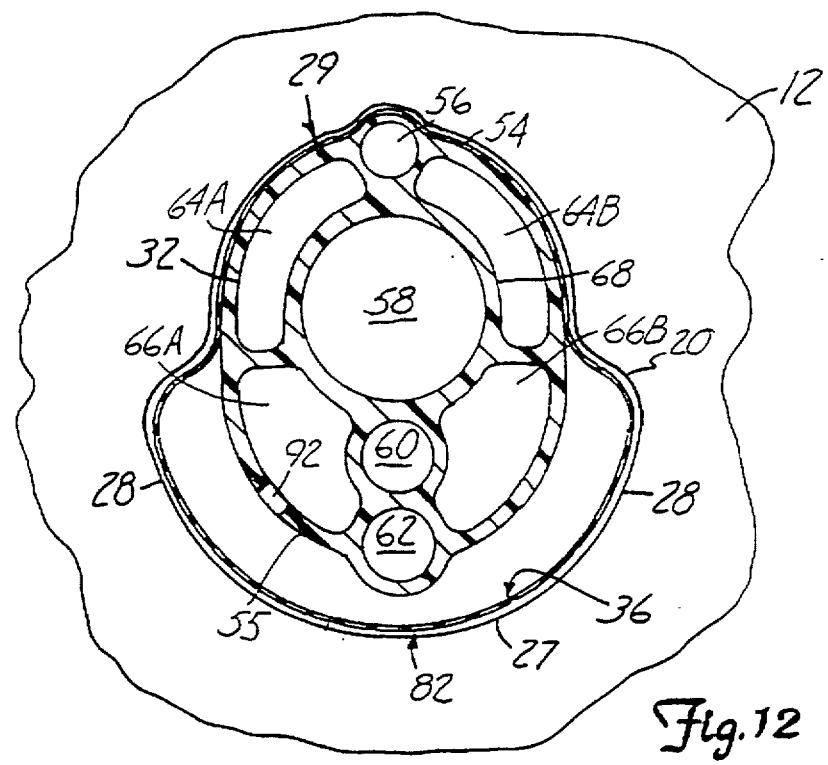
FIG. 12 is a sectional view of a urethra of FIG. 1 as seen along the lines 12—12 with a catheter of the present invention positioned therein.

Upon inflation of cooling balloon 36, expandable portion 82 of cooling balloon 36 establishes substantially uniform contact with the prostatic urethral wall, particularly in the region proximal to the verumontanum 24, as shown in FIG. 11. Inflated cooling balloon 36 effectively fills in the recess 25 at the point of angulation 23 proximal to the verumontanum 24. As shown in FIG. 12, prostatic urethra 20 assumes the shape of the inflated cooling balloon 36 and the remainder of catheter shaft 32 thereby establishing substantially intimate wall contact between the catheter 29 and prostatic urethra 20 including contact between expandable portion 82 of cooling balloon 36 and the posterior portion 27 of the prostatic urethra 20. Vertices 28 adjacent to posterior portion 27 temporarily disappear as the prostatic urethra 20 assumes the shape of cooling balloon 36 and shaft 32, thereby facilitating improved wall contact. Cooling balloon 36 also establishes wall contact with other minor recesses or undulations in the wall of the prostatic urethra 20.

With the catheter 29 properly positioned, microwave antenna 35 is energized. Since cooling fluid exhaust lumens 66A, 66B and cooling balloon 36 absorb more microwave energy than cooling fluid intake lumens 64A, 64B, the intensity of the electromagnetic energy delivered by antenna 35 is greater on catheter first side 54 than on catheter second side 55. As a result, a relatively large volume of tissue enveloping the tumorous prostatic tissue within transition zone 100 adjacent catheter first side 54, is heated according to a time and temperature relationship sufficient to effectively necrose the tumorous tissue of prostate 14 which encroaches upon prostatic urethra 20 (causing constriction 15). In comparison, the temperature of prostate tissue adjacent to catheter second side 55 is controlled (e.g., below about 45° C.) to avoid necrosis of posterior tissues including ejaculatory duct 17 and rectum 18. For a complete discussion on the time and temperature relationship for causing necrosis of prostatic tissue, see Dickson et al, Thermosensitivity of Neoplastic Tissues In Vivo, HYPERTHERMIA IN CANCER THERAPY, Chapter 5 (1983).

This selective cooling pattern created by catheter 29 allows a sufficiently high level of microwave energy to be concentrated only in selective locations deep within region 100 (e.g., at least 2 cm) while protecting healthy tissues (e.g., ejaculatory duct 17) from necrosing time/temperature exposure. After a desired amount of microwave energy has been applied to the tumorous tissue within region 100 and the surrounding tissues have been allowed to return to normal body temperature, the cooling system can be turned off thereby permitting deflation of the cooling balloon 36. Once the cooling balloon 36 and retention balloon 37 have been deflated, the catheter 29 can be removed from urethra 10.

The catheter of the present invention permits the application of microwave energy in an urethral environment to ablate tissue lesions located deep (e.g., 2 cm) below a surface of the tissue without causing necrosis of surrounding healthy tissues. This capability is achieved by a combination of features including, amongst others, an efficient antenna design and a microwave energy absorbing system. The antenna used with the present invention minimizes reflective losses, provides good current carrying capability, and has an effective electrical length that can remain consistent despite different physical lengths of the antenna. The microwave energy absorbing system includes a pair of cooling fluid intake lumens, a pair of cooling fluid exhaust lumens and a cooling balloon, which complements the cooling exhaust lumens.

Performing a thermal therapy treatment on a prostate with catheter 29 of the present invention has considerable advantages. Cooling balloon 36 in combination with cooling exhaust lumens 66A, 66B enables cooling fluid within catheter 29 to cool tissues immediately adjacent catheter second side 55 via thermal conduction. At the same time, the cooling fluid within cooling balloon 36 and within cooling exhaust lumens 66A, 66B, absorbs a substantial amount of microwave energy (when microwave antenna 35 within antenna lumen 58 is energized) so that the temperature of tissue adjacent second side 55 of shaft 32 will remain below a necrosing temperature as desired (e.g., below 45° C). In combination, the relatively large dimensions of the cooling balloon 36, and its relative position adjacent a microwave antenna on second side 55 of catheter 29 provides a cooling chamber that protects healthy tissue, (e.g., ejaculatory duct 17) when a microwave antenna within lumen 58 is energized. The position of the cooling balloon 36 (when inflated) also increases the distance between the rectum 18 and a microwave antenna within lumen 58, which substantially limits the amount of microwave energy that is radiated in the direction of rectum 18. Conversely, high levels of microwave energy are directed anteriorly and laterally of the urethra as cooling intake lumens 64A, 64B protect urethra 10 from thermal damage without substantially absorbing microwave radiation directed toward target tissues. This enables tissue in target region 100 (FIG. 11) deep below the urethral wall surface to be adequately necrosed while at the same time preserving healthy tissues on a side of the catheter opposite the target location.

In addition, an inflated cooling balloon 36 urges prostatic urethra 20 into intimate contact with cooling balloon 36 and shaft 32, so that uniform wall contact is achieved between the intima of prostatic urethra 20 and shaft outer surface 53 adjacent catheter first side 54, and between the intima of prostatic urethra 20 and an outer surface of cooling balloon 36 adjacent catheter second side 55. This arrangement minimizes undesired heat damage to the intima of prostatic urethra 20 that otherwise can occur when spacing develops between prostatic urethra 20 and an outer surface of an ablation catheter within prostatic urethra 20. This feature is particularly significant adjacent verumontanum 24 and point of angulation 23 since this location typically corresponds to a stiffest portion of the catheter 29 extending through the prostatic urethra 20. In this location, the cooling balloon 36 can insure wall contact in recess 25 proximal to verumontanum 24 to avoid blanching of this section of the urethral wall.

To facilitate this uniform wall contact in prostatic urethra 20 proximal to verumontanum 24, cooling balloon 36 has a length less than the entire length of prostatic urethra 20 and preferably a length equal to or less than a length of prostatic urethra 20 proximal to verumontanum 24. This preferred length accentuates improved wall contact in this proximal segment of the prostatic urethra 20 to improve cooling during a thermal therapy session without unnecessarily affecting distal segment 22 of prostatic urethra 20. This preferred length insures uniform wall contact in recess 25 proximal to verumontanum 24 without distorting the general shape of urethra 20 along its length and without compressing tissue surrounding prostatic urethra 20. A uniform intimal contact achieved via cooling balloon 36 permits greater intraprostatic temperatures to be applied to necrose tumorous tissue since greater amounts of microwave energy can be radiated without pain to the patient and with less risk of damaging the wall of urethra.

In addition, cooling balloon 36 accentuates thermal conduction between cooling fluid within cooling balloon 36 and the urethral wall since cooling balloon 36 has a wall thickness less than the cooling exhaust lumens 66A, 66B. This feature places cooling fluid into closer contact with prostatic urethra 20 thereby improving heat transfer away from the urethral wall to further protect urethra 10.

The cooling balloon is capable of being deflated as well as inflated. When deflated, the cooling balloon gives the catheter an overall low profile which facilitates insertion and advancement of the catheter through the urethra or for deployment in distally remote conduits. Moreover, cooling balloon 36 surrounds catheter shaft 32 with expandable portion 82 being the only portion of cooling balloon 36 spaced from catheter outer surface 53. This arrangement permits deflated cooling balloon 36 to have a low profile making cooling balloon 36 highly resistant to separation from the catheter shaft 32 and facilitating rotation of catheter 28 within urethra 10. This arrangement also simplifies or eliminates the need for an elaborate system to wrap balloon 36 in deflated state.

Alternative embodiments of a catheter of the present invention are illustrated in FIGS. 13–19. Catheter 160 shown in FIG. 13 has all the attributes and features of catheter 29 shown in FIGS. 1–12 except that catheter 160 includes a modified structure for communication between cooling exhaust lumens and a cooling balloon. Specifically, instead of the structure shown in FIG. 10, catheter 160 shown in FIG. 13 includes catheter shaft 161 having cooling exhaust lumens 166A and 166B, cooling balloon 168, and a first pair of holes 170A, 170B and a second pair of holes 172A, 172B. An outer wall of cooling exhaust lumen 166A includes holes 170A and 172A, which permit communication between cooling exhaust lumen 166A and an interior of cooling balloon 168. An outer wall of cooling exhaust lumen 166B includes holes 170B and 172B which permit communication between an interior of cooling balloon 168 and cooling exhaust lumen 166B. Cooling fluid enters cooling balloon 168 through holes 170A, 170B and exits cooling balloon 168 through holes 172A, 172B.

Figure 14:
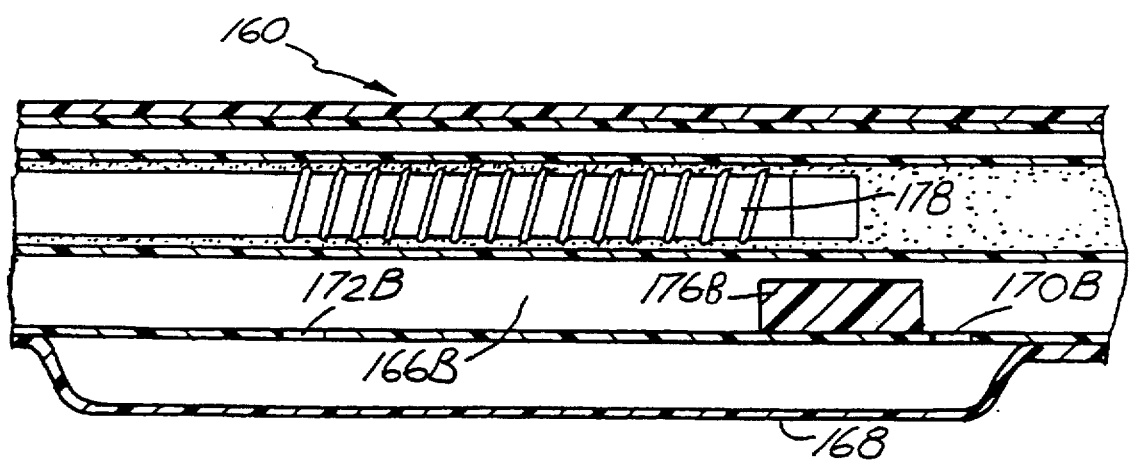
FIG. 14 is a sectional view of FIG. 13 as taken along lines 14—14.

Catheter 160 further includes restrictor 176A located between holes 170A and 172A and restrictor 176B between holes 170B and 172B, as shown in FIG. 14. For illustration purposes, only restrictor 176B located between holes 170B and 172B is shown. Restrictor 176B is positioned on an outer wall of cooling exhaust lumen 166B at a location selected to create a pressure differential between holes 170B, 172B thereby causing passive inflation and active circulation of fluid through cooling balloon 168. Restrictor 176B as shown in FIG. 14, is preferably located immediately adjacent hole 170B and proximal to antenna 178 so that the restrictor 176B does not affect a near field radiation emitted by the antenna 178. However, the restrictor 176B can be located at a more distal location adjacent the antenna 178 if desired. Restrictor 176B is formed and added to cooling exhaust lumen 166B by depositing adhesive on an inner surface of an outer wall of cooling exhaust lumen 166B at a desired location. Restrictor 176A is situated similar to restrictor 176B except being located between holes 170A and 172A in cooling exhaust lumen 166A.

In use, cooling fluid passing through cooling exhaust lumens 166A, 166B enters cooling balloon 168 through holes 170A and 170B thereby permitting passive inflation of cooling balloon 168. Restrictors 176A and 176B accentuate passive inflation of cooling balloon 168 and circulation of fluid therethrough by creating a pressure differential between holes 170A and 172A and between holes 170B and 172B. Holes 172A and 172B permit fluid to exit cooling balloon 168 into cooling exhaust lumens 166A and 166B for recirculation through a cooling system of catheter 160 (not shown).

Figure 15:
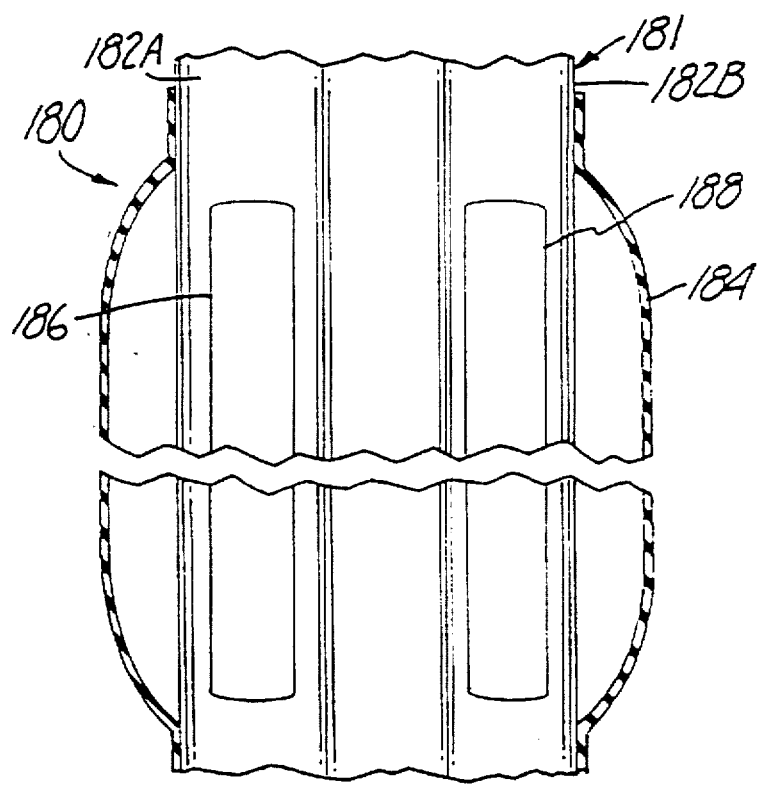
FIG. 15 is a plan view of a second side of the catheter shaft shown in FIGS. 9A and 9B with a balloon portion removed and as taken along lines 10—10 except illustrating an alternate embodiment of cooling exhaust lumens of the catheter of the present invention.

FIG. 15 shows another modified catheter 180 of the present invention. Catheter 180 has all the attributes and features of catheter 29 shown in FIGS. 1–12 except that catheter 180 also includes a modified structure for communication between cooling exhaust lumens and cooling balloon 184.

Specifically, instead of the structure shown in FIG. 10, catheter 180 includes catheter shaft 181 having cooling exhaust lumens 182A and 182B, cooling balloon 184, and a first slot 186 and a second slot 188. Slot 186 is an elongate hole formed in the side wall of catheter shaft defining exhaust lumen 182A while slot 186 is an elongate hole formed in the side wall of catheter shaft defining exhaust lumen 182B. Slot 186 permits unrestricted communication between cooling exhaust lumen 182A and an interior of cooling balloon 184 while slot 188 permits unrestricted communication between cooling exhaust lumen 182B and an interior of cooling balloon 184. This unrestricted communication facilitates relatively turbulent flow of cooling fluid within cooling balloon 184 thereby assuring active circulation of cooling fluid through the cooling balloon 184. Cooling balloon 184 is passively inflated and maintained in that state by controlling the rate of fluid flow into the cooling intake lumens (not shown) and the rate of fluid flow out of the cooling exhaust lumens 182A and 182B.

Figure 16:
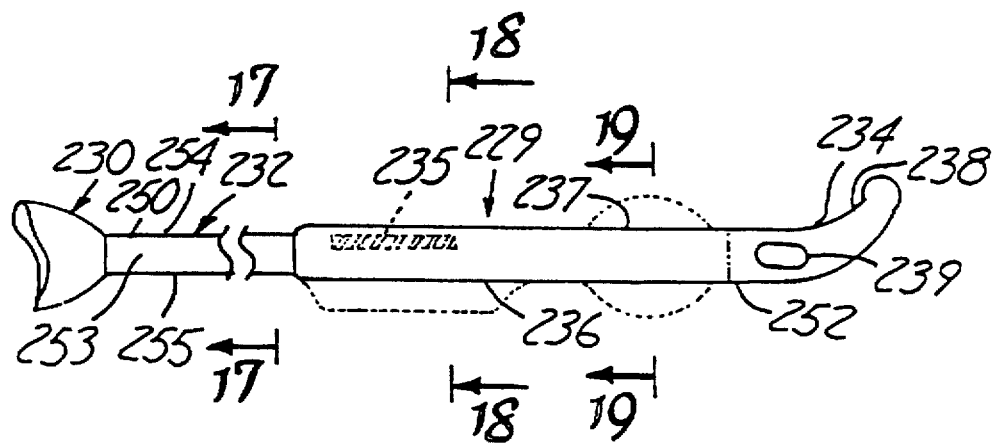
FIG. 16 is a plan view of an alternate embodiment of the urethral catheter of the present invention.

Another embodiment of the present invention is shown in FIGS. 16–19. Catheter 229 is similar to catheter 29 of the present invention (shown in FIGS. 1–14) except that catheter 229 includes a fluid lumen for inflating a cooling balloon that is independent of cooling exhaust lumens of the catheter. As shown in FIG. 16, catheter 229 generally includes multi-port manifold 230, multi-lumen shaft 232, and tip 234, and microwave antenna 235. Tip 234 includes cooling balloon 236, retention balloon 237, and tip portion 238.

Figure 17:
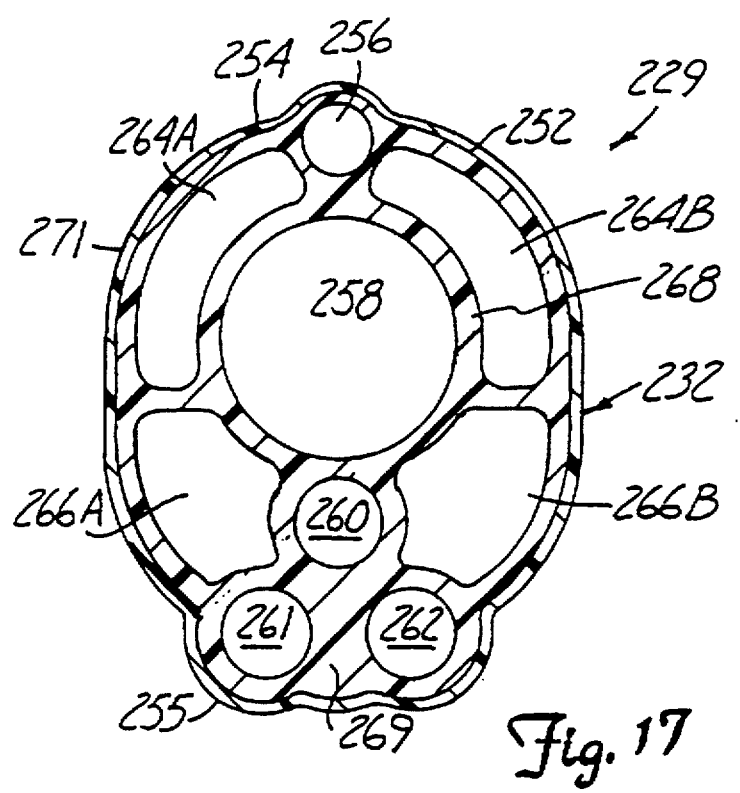
FIG. 17 is a cross-sectional view of the urethral catheter of FIG. 16 taken along line 17—17.

As shown in FIG. 17, multi-lumen shaft 32 includes temperature sensing lumen 256, microwave antenna lumen 258, urine drainage lumen 260, cooling balloon inflation lumen 261, retention balloon inflation lumen 262, cooling fluid intake lumens 264A and 264B, and cooling exhaust lumens 266A and 266B. Lumens 256–266B are similar to the corresponding temperature sensing lumen 56, microwave antenna 58, urine drainage lumen 60, retention balloon inflation lumen 52 and cooling lumens 64A, 64B previously described for catheter 29 in association with FIG. 5. However, unlike catheter 29, catheter 229 further includes a cooling balloon inflation lumen 261 and includes cooling exhaust lumens 266A, 266B which are shaped slightly differently than cooling exhaust lumens 66A, 66B of catheter 29 (FIG. 5).

As shown in FIG. 17, cooling balloon inflation lumen 261 and retention balloon inflation lumen 262 are positioned side by side near second side 255 of shaft 232, generally between urine drainage lumen 260 and second side 255. Both cooling balloon inflation lumen 261 and retention balloon inflation lumen 262 preferably have a generally circular cross-sectional shape defined by catheter wall 268 and preferably have a diameter of about 0.040 inches. Cooling balloon inflation lumen 261 communicates with an inflation port in manifold 230 to permit inflation and deflation of cooling balloon 236. Retention balloon inflation lumen 262 communicates with an inflation port in manifold 230 to permit inflation and deflation of retention balloon 237.

Cooling fluid intake lumens 264A, 264B are positioned adjacent shaft first side 254 and have all the attributes and features of cooling intake lumens 64A, 64B (FIG. 5). Cooling fluid exhaust lumens 266A, 266B are positioned adjacent shaft second side 255 and have all the attributes and features of cooling exhaust lumens 66A, 66B except having a smaller transverse cross-sectional area to accommodate side by side inflation lumens 261 and 262. Cooling exhaust lumens 266A, 266B preferably have a radial thickness greater than a radial thickness of the cooling intake lumens 264A, 264B. In addition, cooling exhaust lumens 266A, 266B lack holes in their outer walls similar to holes 90 and 92 in cooling lumens 66A, 66B. (FIGS. 8A, 8B).

Cooling fluid intake lumens 264A and 264B communicate with cooling exhaust lumens 266A and 266B, respectively, near proximal shaft end 252 of catheter shaft 232 adjacent retention balloon 237. Cooling intake lumens 264A and 264B and cooling exhaust lumens 266A and 266B cooperate with a cooling system via manifold 230 to provide a selectively controlled flow of fluid from cooling intake lumens 264A, 264B into cooling exhaust lumens 266A, and 266B during a treatment session. Fluid contained within exhaust lumens 266A and 266B selectively absorbs a portion of microwave energy emitted by a microwave antenna within antenna lumen 258 and cools tissue surrounding shaft second side 255 to aid in controlling the temperature of tissue adjacent catheter shaft second side 255 below necrosing levels (e.g., below 45° C.). The cooling exhaust lumens 266A,266B are relatively larger in cross section than the cooling intake lumens 264A,264B resulting in more microwave energy being absorbed and greater tissue cooling on the second side 255 of the catheter 229 adjacent the cooling exhaust lumens 266A,266B. This arrangement achieves a desired preferential heating pattern surrounding a microwave antenna while catheter shaft 232 is within urethra 10.

Figure 18:
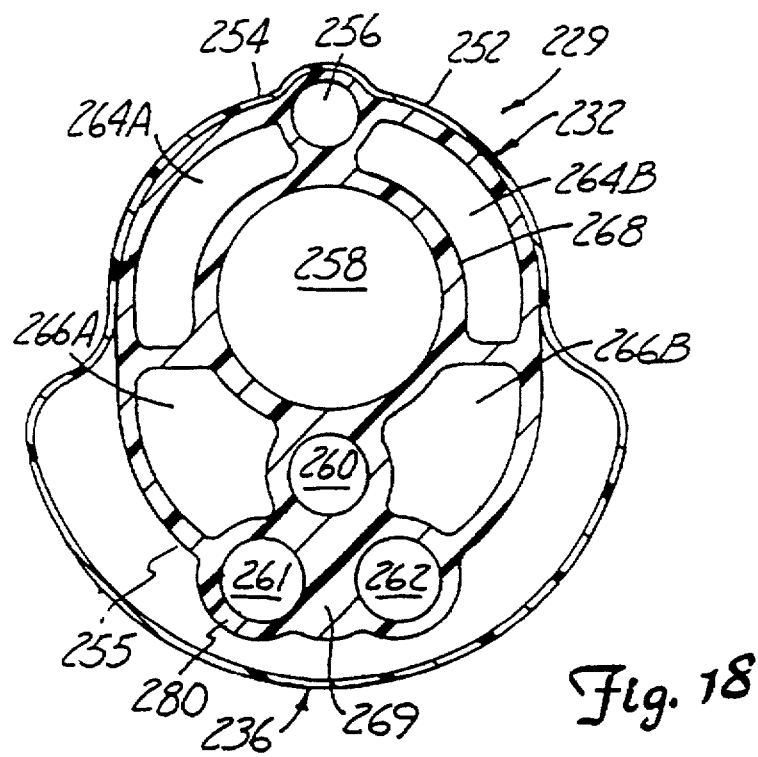
FIG. 18 is a cross-sectional view of the catheter of FIG. 16 taken along lines 18—18.
Figure 19:
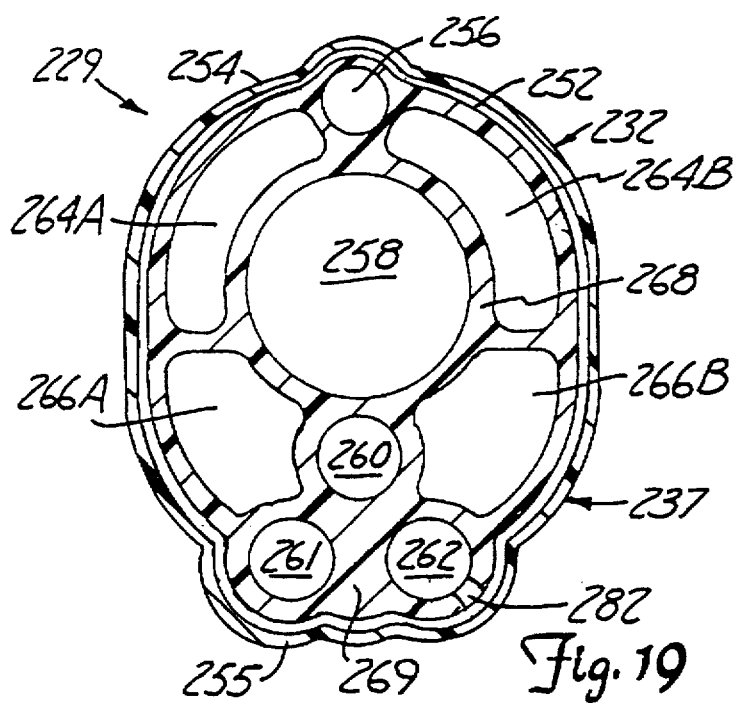
FIG. 19 is a cross-sectional view of the catheter of FIG. 16 taken along lines 19—19.

As further shown in FIG. 18, cooling balloon 236 surrounds shaft outer surface 253 on shaft second side 255. Cooling balloon 236 has all the attributes and features of cooling balloon 36 of catheter 29 (as previously described in association with FIGS. 1–12). As shown in FIGS. 18, side wall 268 of catheter shaft 232 that defines cooling balloon inflation lumen 261 includes hole 280. As shown in FIG. 19, side wall 268 defining retention balloon inflation lumen 262 includes hole 282 (FIG. 22). Hole 280 permits communication between cooling balloon inflation lumen 261 and an interior of cooling balloon 236 (shown inflated in FIG. 18) while hole 282 permits communication between retention balloon inflation lumen 262 and an interior of retention balloon 237 (shown deflated in FIG. 19). Accordingly, cooling balloon 236 is filled and inflated by the introduction of cooling fluid from cooling balloon inflation lumen 261 through hole 280 while retention balloon 237 is filled and inflated by the introduction of cooling fluid from cooling balloon inflation lumen 262 through hole 282.

Cooling inflation lumen 261 is independent of cooling exhaust lumens 266A, 266B enabling cooling balloon 236 to be inflated and deflated independently of fluid flow within cooling exhaust lumens 266A, 266B. This relationship provides an additional means of contacting and cooling the urethra while permitting independent control of cooling fluid within cooling lumens 264, 264B, and 266A, 266B. However, since cooling balloon 236 and cooling inflation lumen 261 do not permit recirculation of fluid within balloon 236 while inflated, fluid within cooling exhaust lumens 266A, 266B are relied upon to carry heat away from cooling fluid within cooling balloon 236 via thermal conduction.

Although the present invention has been described with reference to preferred embodiments, workers skilled in the art will recognize that changes may be made in form and detail without departing from the spirit and scope of the invention.

What is claimed is:

1. An intraurethral catheter for microwave thermal therapy comprising:
    an elongate shaft having a first end, a second end, an outer surface and a plurality of lumens which extend between the first end and the second end of the shaft, the plurality of lumens including:
    an antenna lumen; and
    a plurality of fluid flow lumens arranged about the antenna lumen and
    a balloon connected to the outer surface of the elongate shaft along a portion of the shaft, the balloon having an inflatable portion which partially surrounds the antenna lumen and which is in fluid communication with at least one of the plurality of fluid flow lumens.

2. The intraurethral catheter of claim 1 wherein the plurality of fluid flow lumens further comprises a first and second pair of fluid flow lumens and the second pair of lumens has a transverse cross-sectional area substantially greater than a transverse cross-sectional area of the first pair of lumens.

3. The intraurethral catheter of claim 2 wherein the balloon is arranged so that the inflatable portion of the balloon is adjacent the second pair of cooling lumens.

4. The intraurethral catheter of claim 3 wherein an inner wall of the inflatable portion of the balloon is common with a wall defining an outer wall of the second pair of fluid flow lumens so that a majority of the inflatable portion of the balloon is immediately adjacent the second pair of fluid flow lumens.

5. The intraurethral catheter of claim 1, and further comprising an electromagnetic radiation antenna within a portion of the antenna lumen of the shaft, the portion of the antenna lumen being adjacent to the balloon.

6. The intraurethral catheter of claim 5 wherein the balloon has a length greater than a length of the portion of the antenna lumen which contains the antenna.

7. The intraurethral catheter of claim 5 wherein the balloon has a length less than a length of the portion of the antenna lumen which contains the antenna.

8. The intraurethral catheter of claim 1 wherein the balloon has a length substantially less than an entire length of a prostatic urethra.

9. The intraurethral catheter of claim 8 wherein the balloon has a length substantially equal to a length of the prostatic urethra proximal to a verumontanum of the prostatic urethra.

10. The intraurethral catheter of claim 1 wherein the antenna lumen is adapted to prevent fluid communication between the antenna lumen and the fluid flow lumens and between the antenna lumen and the balloon.

11. An intraurethral catheter for microwave thermal therapy comprising:
    an elongate shaft having a first end, a second end, an outer surface and a plurality of lumens which extend between the first end and the second end of the shaft, the plurality of lumens including:
    an antenna lumen;
    a plurality of fluid flow lumens arranged about the antenna lumen; and
    an inflation lumen; and
    a balloon connected to the outer surface of the elongate shaft along a portion of the shaft, the balloon having an inflatable portion which partially surrounds the antenna lumen and which is in fluid communication with the inflation lumen.

12. A device for treatment of BPH comprising:
    an intraurethral catheter adapted to be inserted into a urethra, the catheter having an outer surface, a first end, a second end, a first side for orientation toward a first wall of the urethra, and a second side for orientation toward a second wall of the urethra;
    radiating means within the catheter for producing an emission capable of necrosing target prostatic tissue beyond a surface of the first and second walls of the urethra;
    means within the catheter disposed between the radiating means and the outer surface of the catheter on both the first and second sides of the catheter for preventing necrosis of the surface of the first and second urethral walls; and a balloon positioned along a portion of the catheter adjacent to the radiating means the balloon being connected to the outer surface of the catheter and having an inflatable portion partially surrounding the radiation means on the second side of the catheter in fluid communication with the means for preventing necrosis of the surface of the first and second urethral walls.

13. The device of claim 12 wherein the balloon has a length substantially less than an entire length of a prostatic urethra.

14. The device of claim 13 wherein the balloon has a length substantially equal to a length of the prostatic urethra proximal to a verumontanum of the prostatic urethra.

15. An intraurethral catheter for microwave therapy comprising:

an elongate shaft having a first end, a second end, an outer surface, and a plurality of lumens extending between the first end and the second end, the plurality of lumens including:
 an antenna lumen; and
 a first fluid flow lumen and a second fluid flow lumen arranged in a side by side relationship and partially surrounding the antenna lumen; and
a balloon connected to the outer surface of the elongate shaft along a portion of the shaft the balloon having an inflatable portion which partially surrounds the antenna lumen and which is in fluid communication with the second fluid flow lumen.

16. The intraurethral catheter of claim 15 wherein an inner wall of the inflatable portion of the balloon is common with a wall defining an outer wall of the second fluid flow lumen so that a majority of the inflatable portion of the balloon is immediately adjacent the second fluid flow lumen.

17. A method for treating diseased tissue adjacent a conduit comprising:

inserting a catheter into a body conduit system including a microwave antenna disposed within an antenna lumen, a plurality of fluid flow lumens substantially surrounding the antenna lumen and a balloon connected to an outer surface of the catheter along a portion of the catheter and having an inflatable portion which partially surrounds the antenna lumen, the balloon being in fluid communication with the fluid flow lumens;

advancing the catheter through the conduit system with the balloon in its deflated state until the microwave antenna is adjacent a diseased portion of tissue adjacent the conduit;

positioning the catheter so that a first side of the catheter is immediately adjacent the tissue to be treated and a second side of the catheter is adjacent healthy tissue;

inflating the inflatable portion of the balloon so that the balloon established substantially uniform wall contact between the outer surface of the catheter and the bodily conduit without distorting a shape of the bodily conduit along its entire length and cools a surface of the bodily conduit; and heating a portion of tissue beyond the surface of the bodily conduit with microwave energy from the microwave antenna at a power range and for a time sufficient to necrose the tissue portion while cooling the conduit surface adjacent the first side of the catheter with fluid flowing through the fluid flow lumens and cooling the conduit surface adjacent the second side of the catheter with fluid flowing through the balloon and the fluid flow lumens.

18. A device for treatment of BPH comprising:

an intraurethral catheter adapted to be inserted into a urethra, the catheter having an outer surface, a first end, a second end, a first side for orientation toward a first wall of the urethra, and a second side for orientation toward a second wall of the urethra;

radiating means within the catheter for producing an emission capable of necrosing target prostatic tissue beyond a surface of the first and second walls of the urethra;

first cooling means within the catheter disposed between the radiating means and the outer surface of the catheter on both the first side and the second side of the catheter for cooling the urethra and for absorbing a first amount of the emission; and second cooling means partially surrounding the radiating means on the second side of the catheter for cooling the urethra without absorbing the emission.

19. The device of claim 18 wherein the emission is a microwave emission and the intraurethral catheter further comprises:

an inflation lumen for supplying a non-microwave-absorbing cooling fluid to the second cooling means.

20. A device for treatment of BPH comprising:

an intraurethral catheter adapted to be inserted into a urethra, the catheter having an outer surface, a first end, a second end, a first side for orientation toward a first wall of the urethra, and a second side for orientation toward a second wall of the urethra;

radiating means within the catheter for producing an emission capable of necrosing target prostatic tissue beyond a surface of the first and second walls of the urethra;

first cooing means within the catheter disposed between the radiating means and the outer surface of the catheter on the first side of the catheter for cooling the urethra and for absorbing a first amount of the emission; and second cooling means partially surrounding around the radiating means on the second side of the catheter and having an inner portion adapted for cooling the urethra and for absorbing a second amount of the emission and an outer portion adapted for cooling the urethra without absorbing the emission.

21. The device of claim 20 wherein the emission is a microwave emission and the intraurethral catheter further comprises:

an inflation lumen for supplying a non-microwave-absorbing cooling fluid to the outer portion of the second cooling means.

22. A method for treating a diseased portion of a prostate comprising:

inserting a catheter into a urethra including a microwave antenna disposed within an antenna lumen, a plurality of fluid flow lumens substantially surrounding the antenna lumen and a balloon connected to an outer surface of the catheter along a portion of the catheter and having an inflatable portion which partially surrounds the antenna lumen, the balloon being in fluid communication with the fluid flow lumens and having a length substantially equal to a length of the urethra in the prostate proximal to a verumontanum of the urethra in the prostate;

advancing the catheter through the urethra with the balloon in its deflated state until the microwave antenna is adjacent a diseased portion of tissue adjacent the urethra;

positioning the catheter so that a first side of the catheter is immediately adjacent the diseased portion to be treated and a second side of the catheter is adjacent healthy tissue so that upon inflation the inflatable portion of the balloon establishes substantially uniform contact with a wall of the urethra from a point just proximal to the verumontanum of the urethra in the prostate to a point just proximal of a proximal end of the urethra in the prostate;

cooling the urethra by directing cooling fluid to flow through the fluid flow lumens and the balloon to cool the urethra adjacent the first side of the catheter with cooling fluid flowing through the fluid flow lumens and to cool the urethra adjacent the second side of the catheter with cooling fluid flowing through the balloon and the fluid flow lumens; and heating the diseased portion beyond a surface of the urethra with microwave energy from the microwave antenna at a power range and for a time sufficient to necrose the diseased portion.

23. A method for treating a diseased portion of a prostate comprising:

inserting a catheter into a urethra including a microwave antenna disposed within an antenna lumen, a plurality of fluid flow lumens substantially surrounding the antenna lumen and a balloon connected to an outer surface of the catheter along a portion of the catheter and having an inflatable portion which partially surrounds the antenna lumen, the balloon being in fluid communication with the fluid flow lumens and having a length substantially equal to a length of the urethra proximal to a verumontanum of the urethra in the prostate;

advancing the catheter through the urethra with the balloon in its deflated state until the microwave antenna is adjacent a diseased portion of tissue adjacent the urethra;

positioning the catheter so that a first side of the catheter is immediately adjacent the diseased portion to be treated and a second side of the catheter is adjacent healthy tissue;

directing cooling fluid to flow through the fluid flow lumens and the balloon so that the balloon is inflated and causes stretching of the urethra radially establishing substantially uniform contact between the catheter and a wall of the urethra from a point just proximal to the verumontanum of the urethra in the prostate to a point just proximal of a proximal end of the urethra in the prostate; and heating the diseased portion beyond a surface of the urethra with microwave energy from the microwave antenna at a power range and for a time sufficient to necrose the diseased portion while cooling the urethra with the cooling fluid flowing through the fluid flow lumens and the balloon.

24. A device for treatment of BPH comprising:

an intraurethral catheter adapted to be inserted into a urethra, the catheter having an outer surface, a first end, a second end, a first circumferential portion for orientation toward a first portion of a wall of the urethra, and a second circumferential portion for orientation toward a second portion of the wall of the urethra opposite the first portion of the wall of the urethra;

radiation means within the catheter for producing an emission capable of necrosing target prostate tissue spaced from a surface of the wall of the urethra;

first means within the catheter adjacent to the radiation means for preventing necrosis of the surface of the wall of the urethra; and a balloon connected to the outer surface of the catheter adjacent the radiation means, the balloon being configured to inflate on the second circumferential portion of the catheter partially surrounding the radiation means.

25. A device for treatment of BPH comprising:

an intraurethral catheter adapted to be inserted into a urethra, the catheter having an outer surface, a first end, a second end, a first circumferential portion for orientation toward a first portion of a wall of the urethra, and a second circumferential portion for orientation toward a second portion of the wall of the urethra opposite the first portion of the wall of the urethra;

radiation means within the catheter for producing an emission capable of necrosing target prostate tissue spaced from a surface of the wall of the urethra;

first means within the catheter disposed between the radiating means and the outer surface of the catheter at both the first and second circumferential portions for preventing necrosis of the surface of the wall of the urethra; and a balloon connected to the outer surface of the catheter adjacent the radiation means, the balloon defining a chamber partially surrounding the radiation means on the second circumferential portion of the catheter.

* * * * *

UNITED STATES PATENT AND TRADEMARK OFFICE
CERTIFICATE OF CORRECTION

PATENT NO. : 5,800,486
DATED : SEPTEMBER 1, 1998
INVENTOR(S) : SCOTT P. THOME ET AL.

It is certified that error appears in the above-identified patent and that said Letters Patent is hereby corrected as shown below:

Col. 2, line 56, delete "FIG. 1", insert --FIG 11--

Col. 8, line 45, delete "6613", insert --66B--

Col. 15, line 2, after "means", insert --,--

Col. 15, line 26, after second instance of "shaft", insert --,--

Col. 16, Line 39, delete "around"

Signed and Sealed this

Twenty-first Day of September, 1999

Attest:

Q. TODD DICKINSON

*Attesting Officer*    *Acting Commissioner of Patents and Trademarks*